US010107828B2

(12) United States Patent
Hoshizaki (10) Patent No.: US 10,107,828 B2
(45) Date of Patent: Oct. 23, 2018

(54) CLAMP DEVICES FOR RECEIVING A CARTRIDGE AND METHODS FOR USING SAME

(71) Applicant: LIFE TECHNOLOGIES CORPORATION, Carlsbad, CA (US)

(72) Inventor: Jon Hoshizaki, Cupertino, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 15/259,191

(22) Filed: Sep. 8, 2016

(65) Prior Publication Data

US 2017/0065981 A1    Mar. 9, 2017

Related U.S. Application Data

(60) Provisional application No. 62/215,936, filed on Sep. 9, 2015.

(51) Int. Cl.
*G01N 35/00* (2006.01)
*B01L 3/00* (2006.01)
(Continued)

(52) U.S. Cl.
CPC .. *G01N 35/00623* (2013.01); *B01L 3/502715* (2013.01); *B01L 9/527* (2013.01);
(Continued)

(58) Field of Classification Search
CPC ....................................................... G01N 35/00
(Continued)

(56) References Cited

U.S. PATENT DOCUMENTS 5,279,791 A * 1/1994 Aldrich ............ B01L 3/502715
422/404
5,876,675 A * 3/1999 Kennedy ........... B01L 3/502715
204/451
(Continued)

FOREIGN PATENT DOCUMENTS

CA    2931155    7/2015
WO    2017/044527    3/2017

OTHER PUBLICATIONS

PCT/US2016/050624, International Search Report and Written Opinion, dated Nov. 24, 2016, 1-11.
(Continued)

*Primary Examiner* — Arlen Soderquist (57) ABSTRACT

A clamp device includes a frame; a carriage slidably engaged with the frame and including a receptacle to receive a cartridge including fluidics ports and electronic contacts, the carriage slidable between an open position and a closed position; a fluidics interface to engage the fluidics ports of the cartridge when the carriage is in a closed position; an electronic interface to engage the electronic contacts of the cartridge when the carriage is in the closed position; a driver to draw the fluidics interface and the electronic interface together, the cartridge secured between the electronic interface and the fluidics interface; and a sensor system to detect the presence of the cartridge in the receptacle and configured to prevent the driver from drawing the fluidics interface and electronic interface together when the cartridge is absent.

20 Claims, 5 Drawing Sheets

(51) Int. Cl.
  *B01L 9/00* (2006.01)
  *G01N 35/10* (2006.01)
(52) U.S. Cl.
  CPC ... *B01L 2200/025* (2013.01); *B01L 2200/027* (2013.01); *B01L 2200/04* (2013.01); *B01L 2200/141* (2013.01); *B01L 2200/143* (2013.01); *B01L 2300/0627* (2013.01); *B01L 2300/18* (2013.01); *G01N 35/00029* (2013.01); *G01N 35/1095* (2013.01); *G01N 2035/00158* (2013.01)
(58) Field of Classification Search
  USPC ..................................... 422/502–503; 436/50
  See application file for complete search history.

(56) References Cited

U.S. PATENT DOCUMENTS

| | | | | |
|---|---|---|---|---|
| 6,132,685 A | * | 10/2000 | Kercso | G01N 35/028 422/552 |
| 6,632,400 B1 | * | 10/2003 | Brennen | B01L 3/502707 204/452 |
| 7,396,444 B2 | * | 7/2008 | Berndt | B01J 19/0093 204/451 |
| 7,630,063 B2 | * | 12/2009 | Padmanabhan | G01N 15/1484 356/246 |
| 7,980,149 B2 | * | 7/2011 | Godfrey | B01L 9/527 422/544 |
| 8,354,077 B2 | * | 1/2013 | Prak | B01L 9/527 204/403.01 |
| 8,404,198 B2 | * | 3/2013 | Amshey | B01L 3/502715 422/561 |
| 8,940,147 B1 | * | 1/2015 | Bartsch | G01N 27/44791 204/601 |
| 9,399,216 B2 | * | 7/2016 | Samper | B01L 3/502746 |
| 2002/0015667 A1 | * | 2/2002 | Chow | B01L 3/502715 422/502 |
| 2006/0163069 A1 | * | 7/2006 | Prak | B01L 9/527 204/601 |
| 2009/0114044 A1 | * | 5/2009 | Godfrey | B01L 9/527 73/864.91 |
| 2009/0269248 A1 | * | 10/2009 | Falb | B01L 3/5025 422/400 |
| 2014/0319042 A1 | | 10/2014 | Prentice et al. | |
| 2015/0093815 A1 | * | 4/2015 | Kiani | B01L 3/502738 435/287.2 |
| 2015/0111289 A1 | * | 4/2015 | Tsao | B01L 3/502715 435/287.2 |
| 2015/0290644 A1 | * | 10/2015 | Prentice | B01L 3/563 422/502 |

OTHER PUBLICATIONS

PCT/US2016/050624, International Preliminary Examination Report, dated Mar. 22, 2018, 1-11.

* cited by examiner

CLAMP DEVICES FOR RECEIVING A CARTRIDGE AND METHODS FOR USING SAME

CROSS-REFERENCE TO RELATED APPLICATION(S)

This application claims benefit of U.S. Provisional Application No. 62/215,936, filed Sep. 9, 2015, which is incorporated herein by reference in its entirety.

FIELD OF THE DISCLOSURE

This disclosure, in general, relates to clamp devices for interfacing with flow cell sensors.

BACKGROUND

Increasingly, sensor devices are integrating sensors within flow cell designs. Such flow cell designs can guide fluid including an analyte over sensors, such as an array of sensors, to detect the analyte or to detect a reaction incorporating the analyte. When such devices include both an electronic interface and a fluid interface, there is a significant risk of short-circuiting or damaging the electronic interface when fluid drips onto the electronic interface.

Such risk is particularly high when engaging or disengaging the fluid interface. Moreover, when the interface is not engaged, any fluid contacting the electronic interface can significant damage the electronic interface.

As such, an improved clamping device would be desirable.

SUMMARY

In a first aspect, a clamp device includes a frame; a carriage slidably engaged with the frame and including a receptacle to receive a cartridge including fluidics ports and electronic contacts. The carriage is slidable between an open position and a closed position. The clamp device further includes a fluidics interface to engage the fluidics ports of the cartridge when the carriage is in a closed position; an electronic interface to engage the electronic contacts of the cartridge when the carriage is in the closed position; a driver to draw the fluidics interface and the electronic interface together, the cartridge secured between the electronic interface and the fluidics interface; and a sensor system to detect the presence of the cartridge in the receptacle and configured to prevent the driver from drawing the fluidics interface and electronic interface together when the cartridge is absent.

In a second aspect, a clamp device includes a frame; a carriage slidably engaged with the frame and including a receptacle to receive a cartridge including fluidics ports and electronic contacts. The carriage is slidable between an open position and a closed position. The clamp device further includes a fluidics interface to engage the fluidics ports of the cartridge when the carriage is in a closed position; an electronic interface to engage the electronic contacts of the cartridge when the carriage is in the closed position; a first driver to draw the fluidics interface and the electronic interface together, the cartridge secured between the electronic interface and the fluidics interface; a second driver to move the carriage between the open position and the closed position; and a sensor system to detect the presence of the cartridge in the receptacle and configured to prevent the second driver from moving the carriage between the open position and the closed position when the cartridge is absent.

In a third aspect, a method of engaging a cartridge including fluidic ports on a first side and electronic contacts on a second side opposite the first side includes applying the cartridge into a clamp device of any one of the above aspects and examples, motivating the carriage toward a closed position, and detecting the cartridge with the sensor system, the sensor system preventing the driver from drawing the fluidics interface and the electronic interface together in the absence of the device.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

In an exemplary embodiment, a clamp device includes a carriage that is movable between an open position and a closed position. In the open position, the carriage can receive a cartridge having fluidics ports and an electronic interface. In the closed position, a fluidics system can engage the fluidics ports of the cartridge, and a clamp device electronic interface can engage the electronic interface of the cartridge. The clamp device can include one or more drivers to move the carriage or to engage the clamp device fluidics system and electronic interface with the cartridge. In a particular example, the clamp device includes a sensor to sense the presence of the cartridge. A sensor system associated with the sensor can permit or prevent the carriage from moving to the closed position or can prevent the fluidics system and clamp device electronic interface from pinching together to engage the cartridge based on detecting an absence of a cartridge.

In use, the clamp device can receive a cartridge in a receptacle of the carriage when the carriage is in the open position. The carriage can be motivated towards the closed position, for example, manually. A sensor position proximal to the receptacle when the carriage is in the open position or positioned along a path of the cartridge as a carriage moves between the open position and the closed position can detect the presence of the cartridge and control the actions of the drivers that move the carriage between the open position and the closed position or that bring the fluidics interface of the clamp device and the electronic interface of the clamp device together to engage the cartridge. In a particular example in which the sensor is disposed along a path of the cartridge, when the carriage is moved from an open position toward a closed position to a sensing position, the carriage can be moved to the sensing position manually, and depending upon the presence of a cartridge, a driver can be engaged to move the carriage to the closed position from the sensing position.

Figures 1, 2:
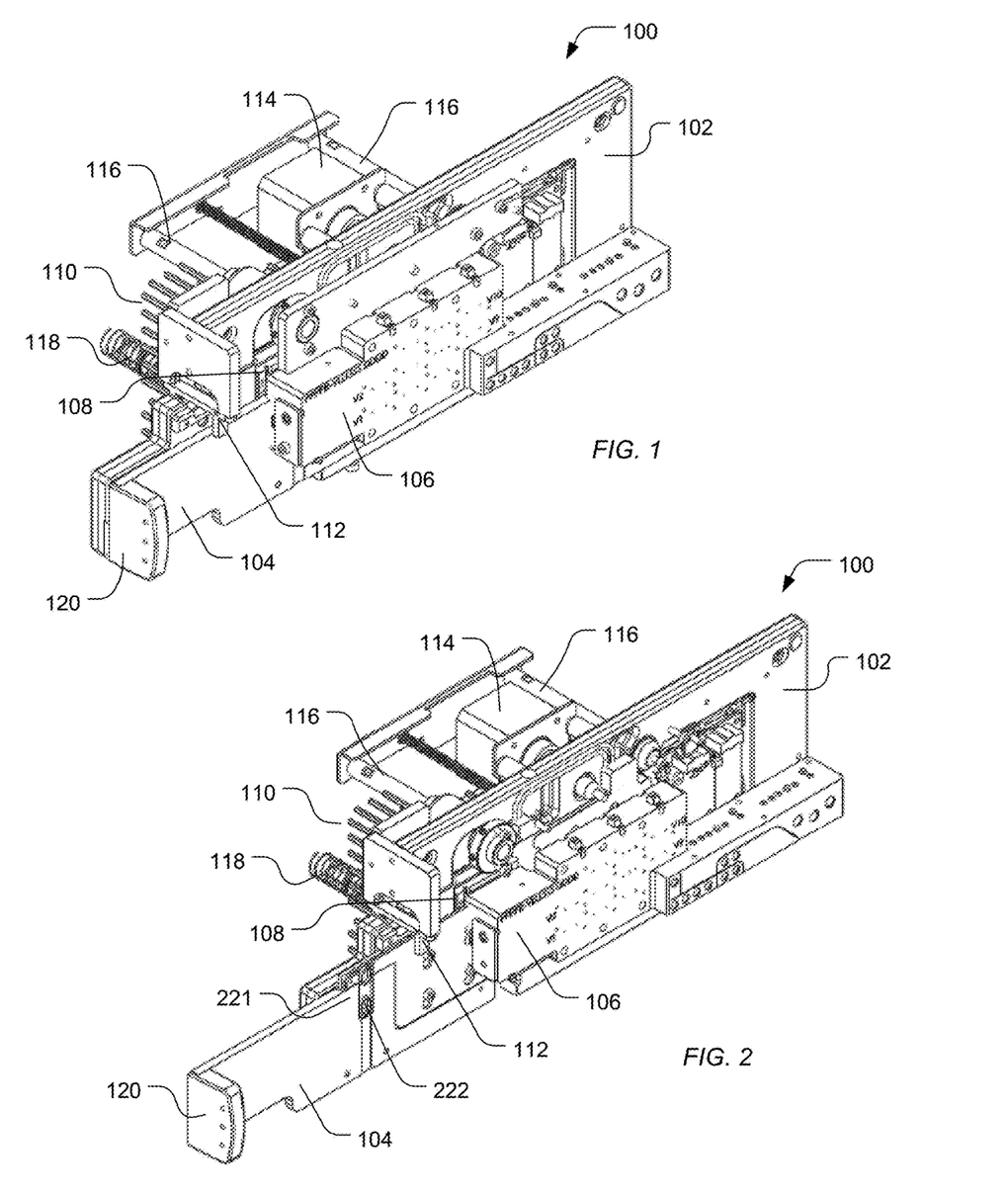
FIG. 1 includes a perspective view illustration of an exemplary clamp device in a closed position.
FIG. 2 includes a perspective view illustration of an exemplary clamp device in an open position.

FIG. 1 includes an illustration of exemplary clamp device 100 that includes a frame 102 and a carriage 104 slidably engaged with the frame 102. The carriage 104 can move between a closed position, as illustrated in FIG. 1, and an open position, as illustrated in FIG. 2. In the open position illustrated in FIG. 2, a receptacle 221 is exposed and can receive a cartridge 222. In an example, the cartridge 222 includes a fluidics interface such as two fluidics ports on a first side and an electronic interface on a second side. The fluidics ports can permit fluidic access to a flow cell within the cartridge 222, and the electronic interface can provide signal inputs and outputs to sensors disposed within the cartridge 222.

As illustrated in FIG. 1 and FIG. 2, the clamp device 100 can include a fluidics system 106 to engage a cartridge when the carriage 104 is a close position. The clamp device 100 can also include an electronic interface 108 positioned opposite the fluidics system 106. When the cartridge 222 is positioned between the fluidics system 106 and the electronic interface 108 of the clamp device 100, the fluidics system 106 and electronic interface 108 can be drawn together to engage the cartridge 222. In an example, a driver 114 can draw the fluidics system 106 and electronic interface 108 together or separate them with the assistance of pistons 116 or springs 118. Optionally, the electronic interface 108 can include a heatsink or Peltier device 110 to control the temperature of the electronic interface 108. For example, an electrothermal Peltier device 110 controls the temperature of the electronic interface.

Figure 3:
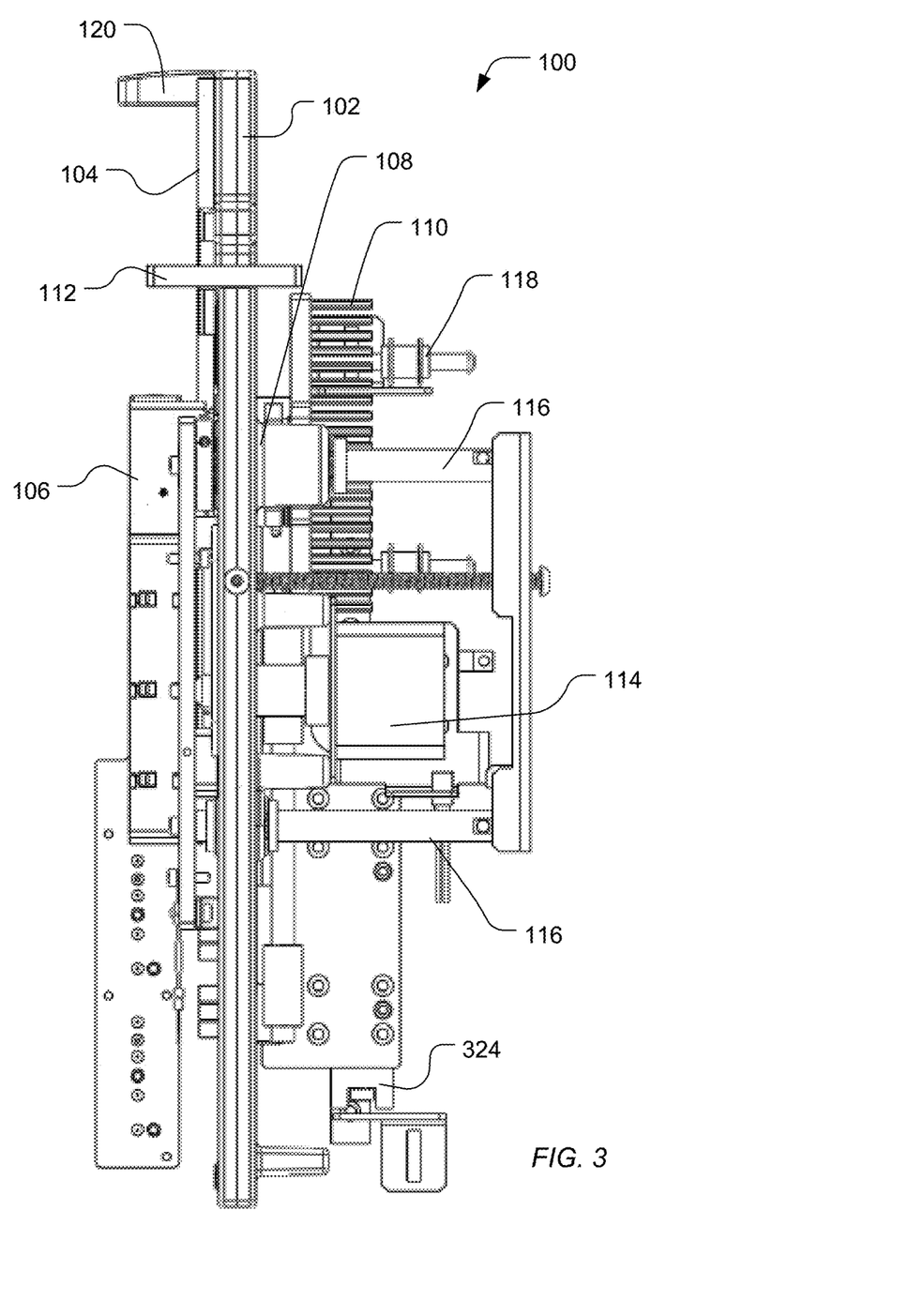
FIG. 3 includes a top view illustration of an exemplary clamp device.

As illustrated in FIG. 3, a driver 324 can be attached to the carriage 104 and can guide the carriage 104 slidably along the frame 102.

Returning to FIG. 1 and FIG. 2, a sensor 112 can be positioned along a path of the carriage 104 between the open position illustrated in FIG. 2 and the closed position illustrated in FIG. 1. Alternatively, the sensor 112 can be positioned proximal to the open position and detect the insertion or the presence of a cartridge 222 in the receptacle 221. When the carriage 104 is moved between the open position to a sensing position at which the sensor 112 detects the presence of the cartridge 222, a sensor 112 as part of a sensing system can determine the absence or presence of the cartridge 222 and activate drivers 324 associated with the carriage 104 to move the carriage 104 to the closed position or the driver 114 to bring the clamp device electronic interface 108 and the fluidics system 106 together when the carriage 104 is in the closed position.

Figure 4:
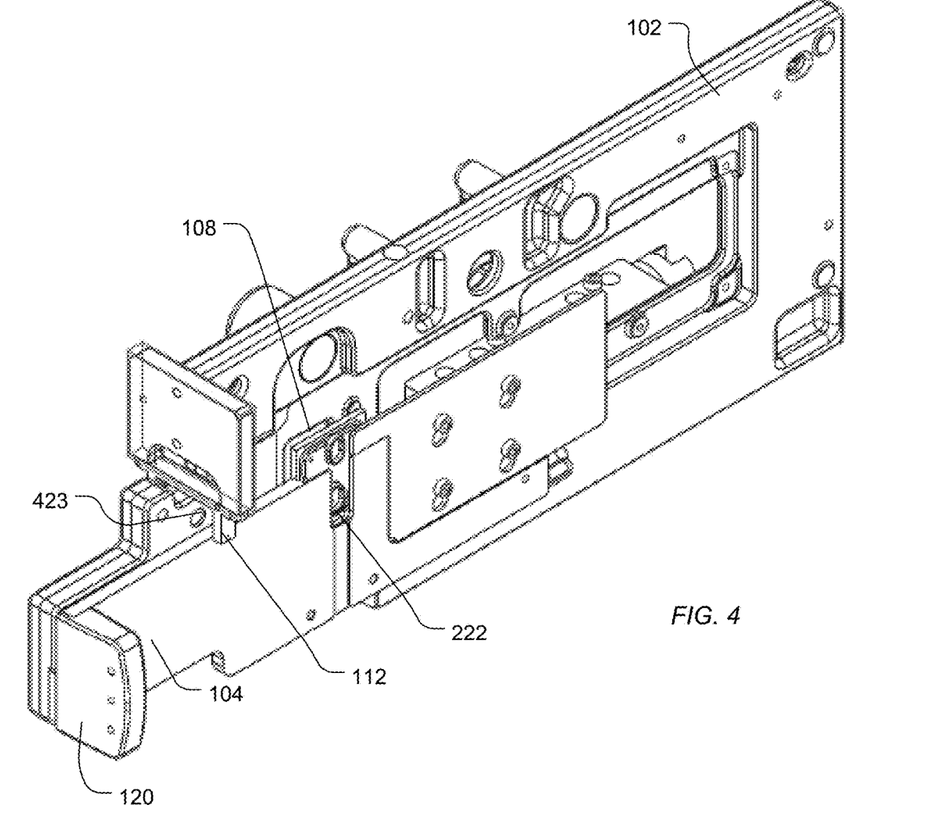
FIG. 4 includes an illustration of a frame and carriage of the exemplary clamp device.

The sensor 112 can be an electronic sensor, an optical sensor, a magnetic sensor, a mechanical switch, or a combination thereof. In a particular example, the sensor 112 is an optical sensor. In a further example, the frame 102 includes an opening 423 through which the optical sensor 112 can project, as illustrated in FIG. 4. As the carriage 104 slides to the sensing position adjacent the sensor 112, the receptacle 221 and optionally the cartridge 222 are positioned to be detected by the sensor 112. In a particular example, the carriage 104 can be manually moved to the sensing position from the open position using a handle 120. When a cartridge 222 is present and detected by the sensor 112, the sensor system can engage a driver to move the carriage 104 to the closed position or can engage a driver 114 to move the fluidics system 106 and the electronic interface 108 of the clamp device 100 together.

Figure 5:
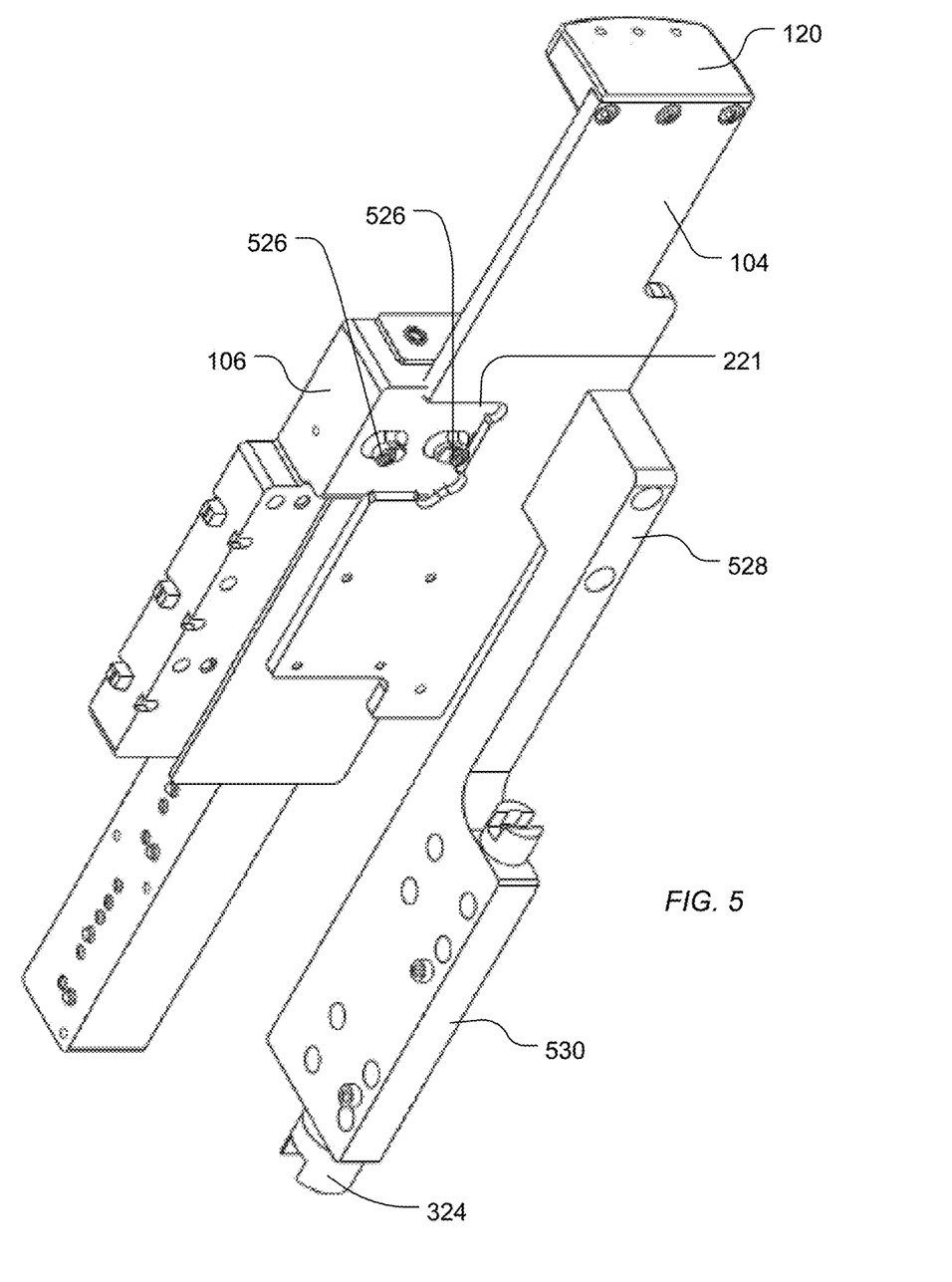
FIG. 5 includes an illustration of a carriage and a fluidics coupling of the exemplary clamp device.

When in the closed position, fluidics ports 526 of the fluidics system 106 can engage the cartridge 222, as illustrated in FIG. 5. In particular, the fluidics ports 526 can include an inlet port and an outlet port that seal to the fluidics interface of the cartridge 222, permitting fluid to pass from the fluidic system 106 through the cartridge 222.

In a further example illustrated in FIG. 5, the carriage 104 can be attached to an arm 528 that includes a mechanism 530 that engages the driver 324 to position the carriage 104 in the closed position or the open position. The mechanism 530 can be a screw-based mechanism. Alternatively, the mechanism can be piston based system, a track system, or a line-based system.

Figure 6:
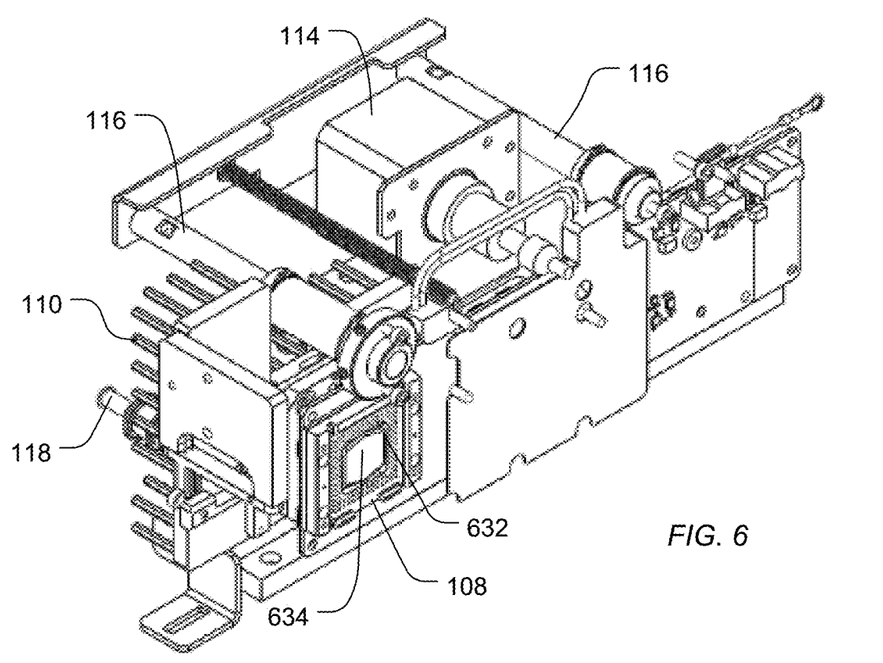
FIG. 6 includes an illustration of an electronic interface of the exemplary clamp device.

FIG. 6 includes an illustration of the electronic interface 108. The electronic interface 108 can include electrical contacts 632. In the illustrated embodiment, the electrical contacts 632 are positioned around the periphery of the electronic interface and match the electronic interface of the cartridge 222. Optionally, a center portion 634 of the electronic interface 108 can be free of electronic contacts 632, and can include a guide to move the cartridge away from the electronic interface 108 when the fluidics system 106 is disengaged. The guide can be a spring-driven piston, an electromechanical device, or a resilient material. For example, the guide is a spring-driven piston acting with a force in an opposite direction of the fluidics interface. The clamp device 100 can also include a mechanism 110 to control the temperature of the electronic interface 108. For example, the system can include a Peltier (electrothermal) device with or without a heatsink 110.

In a first aspect, a clamp device includes a frame; a carriage slidably engaged with the frame and including a receptacle to receive a cartridge including fluidics ports and electronic contacts, the carriage slidable between an open position and a closed position; a fluidics interface to engage the fluidics ports of the cartridge when the carriage is in a closed position; an electronic interface to engage the electronic contacts of the cartridge when the carriage is in the closed position; a driver to draw the fluidics interface and the electronic interface together, the cartridge secured between the electronic interface and the fluidics interface; and a sensor system to detect the presence of the cartridge in the receptacle and configured to prevent the driver from drawing the fluidics interface and electronic interface together when the cartridge is absent.

In an example of the first aspect, the receptacle receives the cartridge in a vertical orientation.

In another example of the first aspect and the above examples, the clamp device further includes a driver to move the carriage between the open position and the closed position In a further example of the first aspect and the above examples, the sensor is an optical sensor.

In an additional example of the first aspect and the above examples, the sensor is positioned in a path of the carriage between the open position and the closed position. For example, the frame includes an opening extending through the frame and positioned along the path of the carriage, the sensor sensing through the opening of the frame.

In another example of the first aspect and the above examples, the clamp device further includes a heat sink in thermal contact with the electronic interface.

In a further example of the first aspect and the above examples, the clamp device further includes an electrothermal device in thermal contact with the electronic interface.

In an additional example of the first aspect and the above examples, the carriage includes a handle.

In a second aspect, a clamp device includes a frame; a carriage slidably engaged with the frame and including a receptacle to receive a cartridge including fluidics ports and electronic contacts, the carriage slidable between an open position and a closed position; a fluidics interface to engage the fluidics ports of the cartridge when the carriage is in a closed position; an electronic interface to engage the electronic contacts of the cartridge when the carriage is in the closed position; a first driver to draw the fluidics interface and the electronic interface together, the cartridge secured between the electronic interface and the fluidics interface; a second driver to move the carriage between the open position and the closed position; and a sensor system to detect the presence of the cartridge in the receptacle and configured to prevent the second driver from moving the carriage between the open position and the closed position when the cartridge is absent.

In an example of the second aspect, the receptacle receives the cartridge in a vertical orientation.

In another example of the second aspect and the above examples, the sensor is an optical sensor.

In a further example of the second aspect and the above examples, the sensor is positioned in a path of the carriage between the open position and the closed position. For example, the frame includes an opening extending through the frame and positioned along the path of the carriage, the sensor sensing through the opening of the frame.

In an additional example of the second aspect and the above examples, the clamp device further includes a heat sink in thermal contact with the electronic interface.

In another example of the second aspect and the above examples, the clamp device further includes an electrothermal device in thermal contact with the electronic interface.

In a further example of the second aspect and the above examples, the carriage includes a handle.

In a third aspect, a method of engaging a cartridge including fluidic ports on a first side and electronic contacts on a second side opposite the first side includes applying the cartridge into a clamp device of any one of the above aspects and examples, motivating the carriage toward a closed position, and detecting the cartridge with the sensor system, the sensor system preventing the driver from drawing the fluidics interface and the electronic interface together in the absence of the device.

In an example of the third aspect, the clamp device further includes a second driver to move the carriage between the open position and the closed position.

In another example of the third aspect, the method further includes heating the electronic interface.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A clamp device comprising:
   a frame;
   a carriage slidably engaged with the frame and including a receptacle to receive a cartridge including fluidics ports and electronic contacts, the carriage slidable between an open position and a closed position;
   a fluidics interface to engage the fluidics ports of the cartridge when the carriage is in a closed position;
   an electronic interface to engage the electronic contacts of the cartridge when the carriage is in the closed position;
   a driver to draw the fluidics interface and the electronic interface together, the cartridge secured between the electronic interface and the fluidics interface; and
   a sensor system to detect the presence of the cartridge in the receptacle and configured to prevent the driver from drawing the fluidics interface and electronic interface together when the cartridge is absent.

2. The clamp device of claim 1, wherein the receptacle receives the cartridge in a vertical orientation.

3. The clamp device of claim 1, further comprising a driver to move the carriage between the open position and the closed position.

4. The clamp device of claim 1, wherein the sensor is an optical sensor.

5. The clamp device of claim 1, wherein the sensor is positioned in a path of the carriage between the open position and the closed position.

6. The clamp device of claim 5, wherein the frame includes an opening extending through the frame and positioned along the path of the carriage, the sensor sensing through the opening of the frame.

7. The clamp device of claim 1, further comprising a heat sink in thermal contact with the electronic interface.

8. The clamp device of claim 1, further comprising an electrothermal device in thermal contact with the electronic interface.

9. The clamp device of claim 1, wherein the carriage includes a handle.

10. A clamp device comprising:
a frame;
a carriage slidably engaged with the frame and including a receptacle to receive a cartridge including fluidics ports and electronic contacts, the carriage slidable between an open position and a closed position;
a fluidics interface to engage the fluidics ports of the cartridge when the carriage is in a closed position;
an electronic interface to engage the electronic contacts of the cartridge when the carriage is in the closed position;
a first driver to draw the fluidics interface and the electronic interface together, the cartridge secured between the electronic interface and the fluidics interface;
a second driver to move the carriage between the open position and the closed position; and
a sensor system to detect the presence of the cartridge in the receptacle and configured to prevent the second driver from moving the carriage between the open position and the closed position when the cartridge is absent.

11. The clamp device of claim 10, wherein the receptacle receives the cartridge in a vertical orientation.

12. The clamp device of claim 10, wherein the sensor is an optical sensor.

13. The clamp device of claim 10, wherein the sensor is positioned in a path of the carriage between the open position and the closed position.

14. The clamp device of claim 13, wherein the frame includes an opening extending through the frame and positioned along the path of the carriage, the sensor sensing through the opening of the frame.

15. The clamp device of claim 10, further comprising a heat sink in thermal contact with the electronic interface.

16. The clamp device of claim 10, further comprising an electrothermal device in thermal contact with the electronic interface.

17. The clamp device of claim 10, wherein the carriage includes a handle.

18. A method of engaging a cartridge including fluidic ports on a first side and electronic contacts on a second side opposite the first side, the method comprising:
applying the cartridge into a clamp device comprising:
a frame;
a carriage slidably engaged with the frame and including a receptacle to receive a cartridge including fluidics ports and electronic contacts, the carriage slidable between an open position and a closed position;
a fluidics interface to engage the fluidics ports of the cartridge when the carriage is in a closed position;
an electronic interface to engage the electronic contacts of the cartridge when the carriage is in the closed position;
a driver to draw the fluidics interface and the electronic interface together, the cartridge secured between the electronic interface and the fluidics interface; and
a sensor system to detect the presence of the cartridge in the receptacle;
motivating the carriage toward a closed position; and
detecting the cartridge with the sensor system, the sensor system preventing the driver from drawing the fluidics interface and the electronic interface together in the absence of the device.

19. The method of claim 18, wherein the clamp device further includes a second driver to move the carriage between the open position and the closed position.

20. The method of claim 18, further comprising heating the electronic interface.

* * * * *